United States Patent [19]
Grant et al.

[11] Patent Number: 5,232,668
[45] Date of Patent: Aug. 3, 1993

[54] TEST STRIP HOLDING AND READING MECHANISM FOR A METER

[75] Inventors: Michael E. Grant, Sand Point, Id.; Russell T. Gray, Brownsburg, Ind.; Mark A. Gregory, Carmel, Ind.; Daniel L. Kennedy, Indianapolis, Ind.; Dino Perin, New Palestine, Ind.; Richard Riedel, Carmel, Ind.; Stephen D. Scopatz, Indianapolis, Ind.; David E. Storvick, Greenwood, Ind.

[73] Assignee: Boehringer Mannheim Corporation, Indianapolis, Ind.

[21] Appl. No.: 661,850

[22] Filed: Feb. 27, 1991

[51] Int. Cl.[5] .................. G01N 21/01; G01N 21/77; G01N 21/78; G01N 21/47
[52] U.S. Cl. .................. 422/82.05; 422/58; 422/68.1; 436/164; 436/165
[58] Field of Search .................. 427/58, 68.1, 82.05; 436/164, 165; 128/770

[56] References Cited

U.S. PATENT DOCUMENTS

| | | | |
|---|---|---|---|
| 3,907,503 | 9/1975 | Betts et al. | 422/67 |
| 3,980,437 | 9/1976 | Kishimoto et al. | 422/55 |
| 4,160,646 | 7/1979 | Furutani et al. | 422/56 X |
| 4,509,859 | 4/1985 | Markart et al. | 422/82.05 X |
| 4,676,653 | 6/1987 | Strohmeier et al. | 356/446 |
| 4,787,398 | 11/1988 | Garcia et al. | 128/770 |
| 4,833,088 | 5/1989 | DeSimone et al. | 435/291 X |
| 4,871,258 | 10/1989 | Herpichboehm et al. | 356/422 |
| 4,934,817 | 6/1990 | Gassenhuber | 422/68.1 X |
| 5,037,614 | 8/1991 | Makita et al. | 422/82.05 X |
| 5,039,615 | 8/1991 | Takahata | 436/165 X |
| 5,053,199 | 10/1991 | Keiser et al. | 422/68.1 |
| 5,059,394 | 10/1991 | Phillips et al. | 422/82.05 X |

FOREIGN PATENT DOCUMENTS

63-269046 11/1988 Japan .................. 422/82.05
387630A2 9/1990 United Kingdom .

OTHER PUBLICATIONS

Accu-Chek ®IIm booklet.

Primary Examiner—James C. Housel
Assistant Examiner—Arlen Soderquist
Attorney, Agent, or Firm—Barnes & Thornburg

[57] ABSTRACT

An instrument for analyzing test strips supporting chemistries which react with a medically significant component of a body fluid to indicate the concentration of the component in the body fluid. The instrument includes a pathway along which radiation is guided from a radiation source to a strip when the strip is inserted into the instrument and along which remission is guided from the strip to a radiation detector. A title provided on the instrument provides a first remission when no strip is inserted into the instrument. The tile is separated from the radiation source by the strip when the strip is inserted into the instrument. The first remission and the strip's remission, respectively, indicate the absence and the presence of the strip in the instrument. The strip also has a surface opposite the chemistry supporting surface characterized by a second strip remission different from the first strip remission. The instrument is capable of determining whether the strip has been inserted into the instrument correctly or backward.

23 Claims, 9 Drawing Sheets

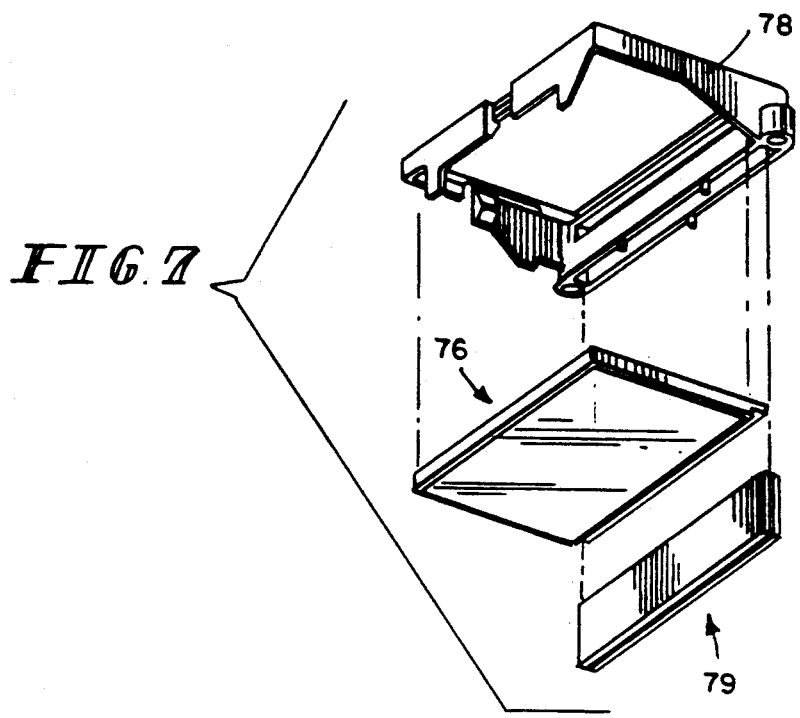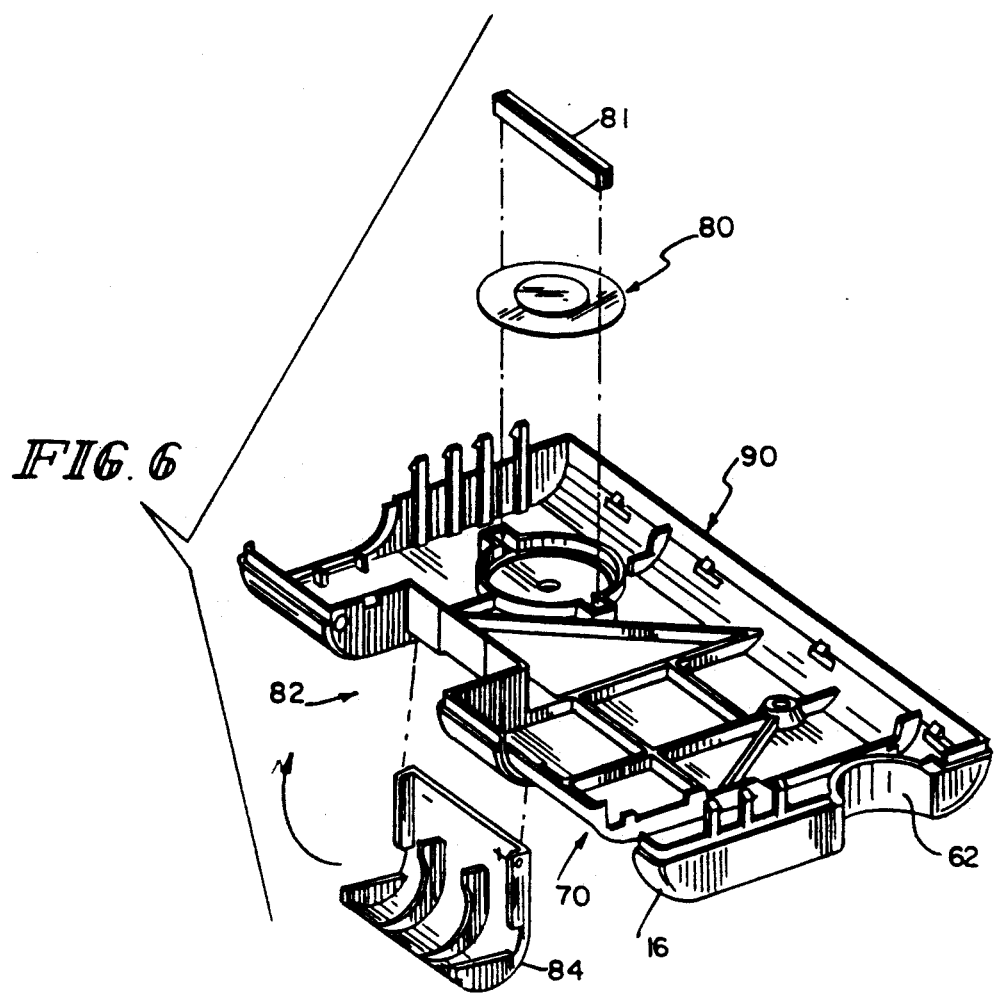

FIG. 9

TEST STRIP HOLDING AND READING MECHANISM FOR A METER

This invention relates to apparatus and methods for reading the concentration of a medically significant component of a biological fluid from a test strip. It is disclosed in the context of an apparatus and a method for reading the concentration of glucose in blood reacted on a test strip with a chemistry with which the strip has previously been treated.

The difficulty many people have with preparing test strips treated with chemistries with bodily fluids such as blood and urine is known. Many users of such strips have poor eyesight owing to diabetes, to age, and to other causes as well. Many users have reduced dexterity or strength in their hands owing to age and to other causes. Frequently these causes are the reasons why these users are testing their bodily fluids for, for example, glucose concentration to begin with.

The problems with such strips only begin with dosing the strips with the bodily fluid or fluids to be analyzed. The chemistries are reactants with the medically significant component(s) of the fluids. These reactants react with the medically significant component(s) resulting typically in some colorimetric indication of the concentration of the medically significant component of the fluid. However, these reactions continue, typically for extended times, until all of the reactants have reacted. Consequently, it is generally necessary to time the reaction of the medically significant component with the strip chemistry so that a colorimetric comparison of the reacted strip chemistry to a standard on a color chart can be made at some established time after the reaction is initiated by depositing the fluid on the strip. Otherwise, if the reaction is not permitted to proceed long enough, or is permitted to proceed too long, the color corresponding to the extent of the reaction will not match the correct standard on the chart.

In addition to potential problems with how long the chemistry on the strip and the medically significant component of the body fluid are permitted to react, there are problems with many of such chemistry systems with how much of the body fluid is applied to the strip, since incorrect amounts of the reactants may affect the validity of the test as adversely as errors in the timing of the reaction. Either way, a false reading, sometimes with dire consequences, will result.

The present invention makes use of an endpoint chemistry system of the type described in U.S. Pat. No. 4,929,545. The disclosure of U.S. Pat. No. 4,929,545 is incorporated herein by reference. The advantages of an endpoint chemistry are clear. For the user who frequently has poor eyesight and/or manual dexterity, there is no need to be concerned about how long the reaction has proceeded. The reaction reaches an endpoint in relatively short order after which there is no significant shift in the color of the reaction products on the strip. In addition, the architecture of the strip described in U.S. Ser. No. 07/661,788, filed Feb. 27, 1991, IMPROVED TEST STRIP, naming as inventors McCroskey, Freitag, Smith, Dean, Secrest and Bouse, and assigned to Boehringer Mannheim Corporation, is such that the proper dose of the body fluid, the biologically significant component of which is to be reacted with the chemistry on the strip, will always be available for the reaction. Any excess is wicked away from the reaction site by the strip architecture. Thus, all the user need do is be sure enough of the bodily fluid is present at the reaction site on the strip to react with the chemistry with which the strip is treated. The disclosure of U.S. Ser. No. 07/661,788 is incorporated herein by reference.

The invention may best be understood by referring to the following detailed description and accompanying drawings which illustrate the invention. In the drawings:

FIGS. 1-8 illustrate exploded perspective views, from various different angles, of various components of an instrument constructed according to the present invention;

FIG. 9 illustrates a partly block and partly schematic circuit diagram of the electric circuit of the instrument illustrated in FIGS. 1-8;

Figure 1:
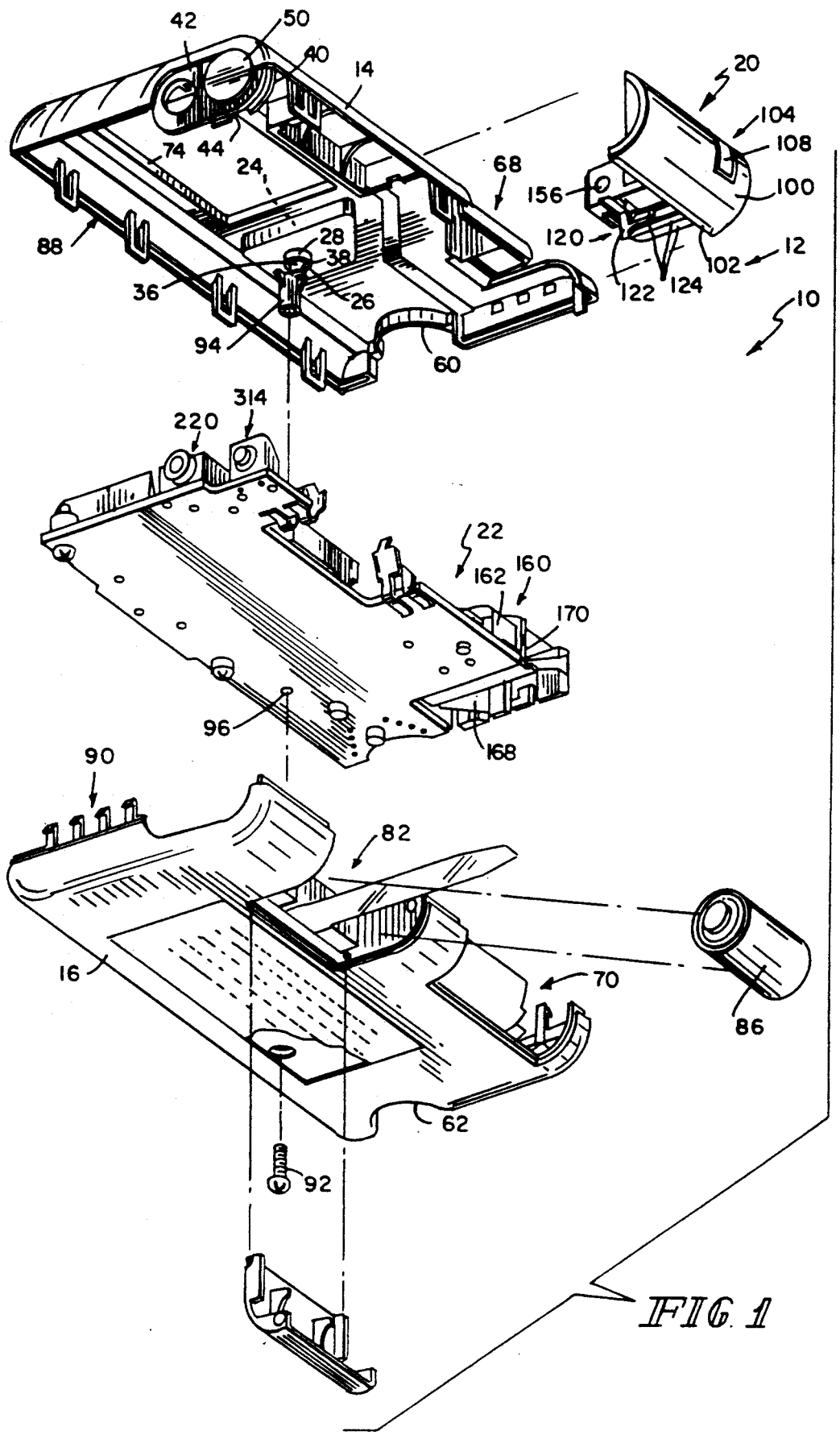
Figure 8:
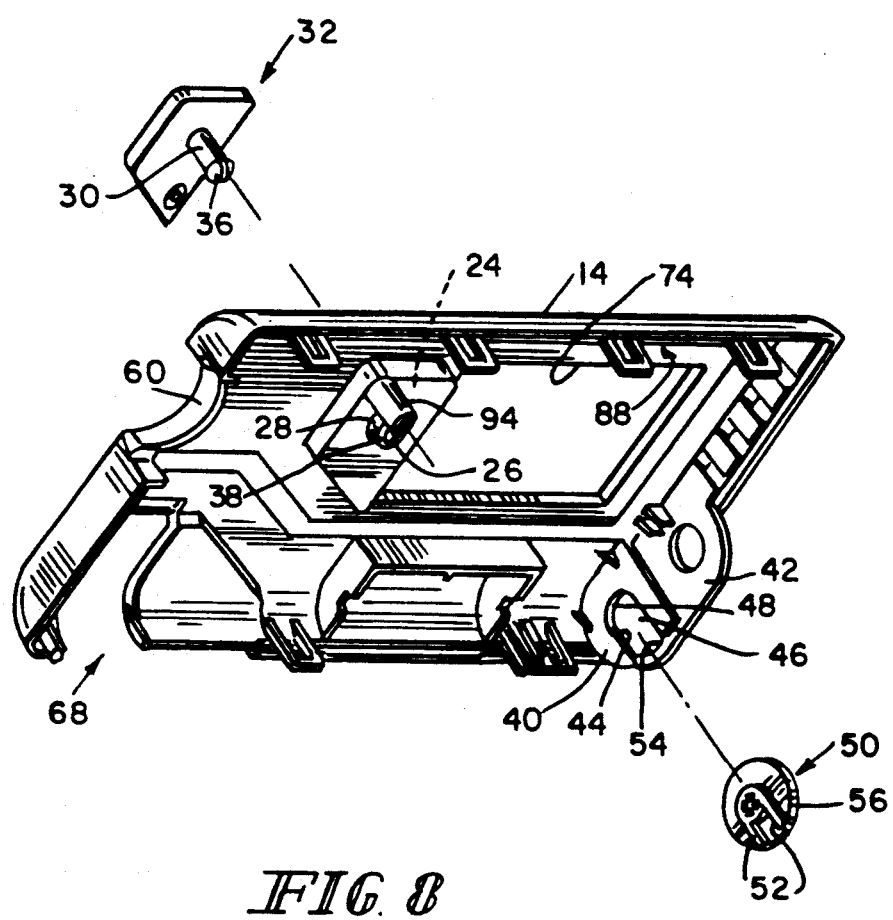
Figure 9:
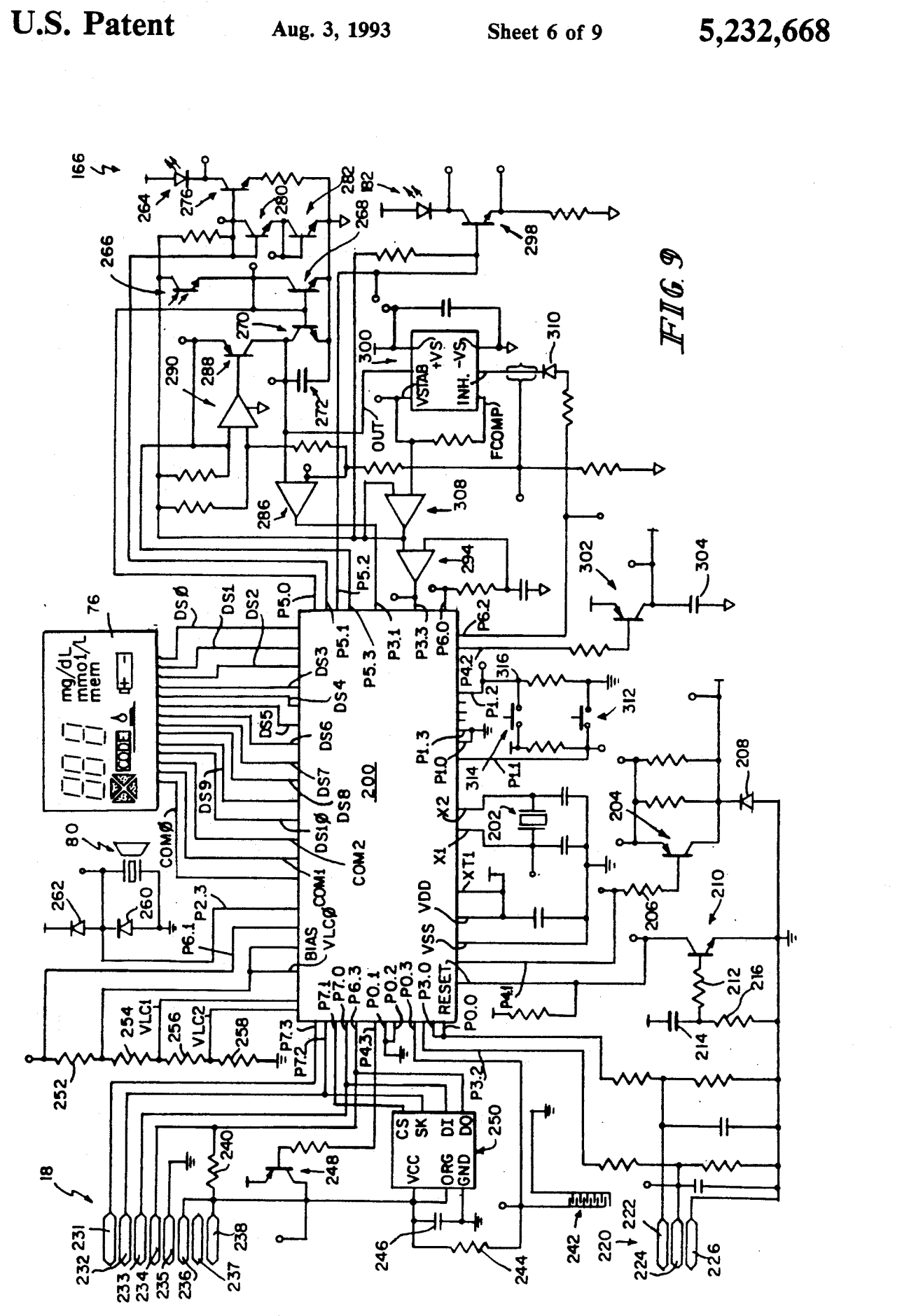

Referring now to FIGS. 1 and 8, an instrument 10 according to the invention includes a case 12 having a front portion 14, a rear portion 16, a key housing portion 18 and a strip carrier holder portion 20. A printed circuit board 22, the contents of which will be considered in more detail in the discussion of FIG. 9, is sandwiched generally between the front and rear portions 14, 16, respectively. Front portion 14 includes a relief 24 of generally trapezoidal configuration at the center of which is a generally circular opening 26. A generally right circular cylindrical stem 28 extends downwardly from the underside of front portion 14 beneath opening 26. This stem 28 slidably receives a stem 30 provided on the back of an ON/OFF button 32 of the same shape as relief 24. The lower end of stem 30 is split axially and somewhat frustoconical in configuration so that button 32 is captured in relief 24 when stem 30 is pushed into opening 26 until the split, frustoconical end 36 of stem 30 clears the bottom end 38 of stem 28. The portion of stem 30 above end 36 is somewhat longer than stem 28 so that some movement of button 32 vertically in relief 24 is possible.

Front casing portion 14 also includes a wall 40 inside of, and parallel with, a region 42 of an end wall thereof. Wall 40 includes a vertically extending groove 44 open at its bottom 46 and with a semicircular top 48. A memory button 50 has ribs 52 on its back wall spaced apart slightly less than the width of groove 44. Button 50 excluding ribs 52 is slightly thicker than the space between wall 40 and region 42. The flexible resin construction of front portion 14 and a circular opening 54 of slightly larger diameter than button 50 in region 42 permits the wall 40 to flex away from region 42 as button 50 is forced into the space between them and snaps into place protruding through opening 54. A flange 56 on button 50 keeps it from going all the way through opening 54 and falling from front portion 14.

Figure 2:
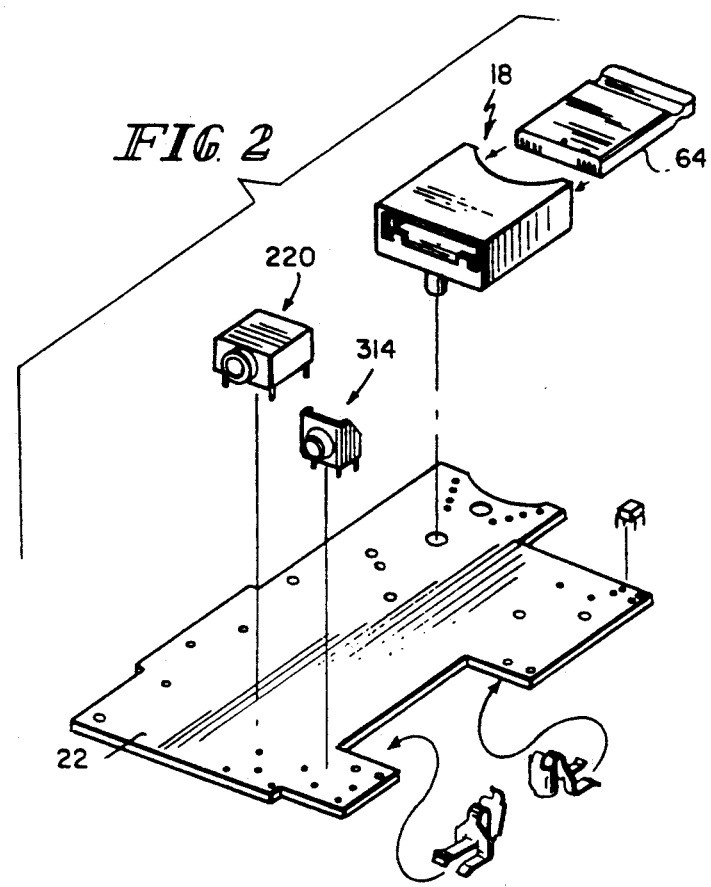
Figure 3:
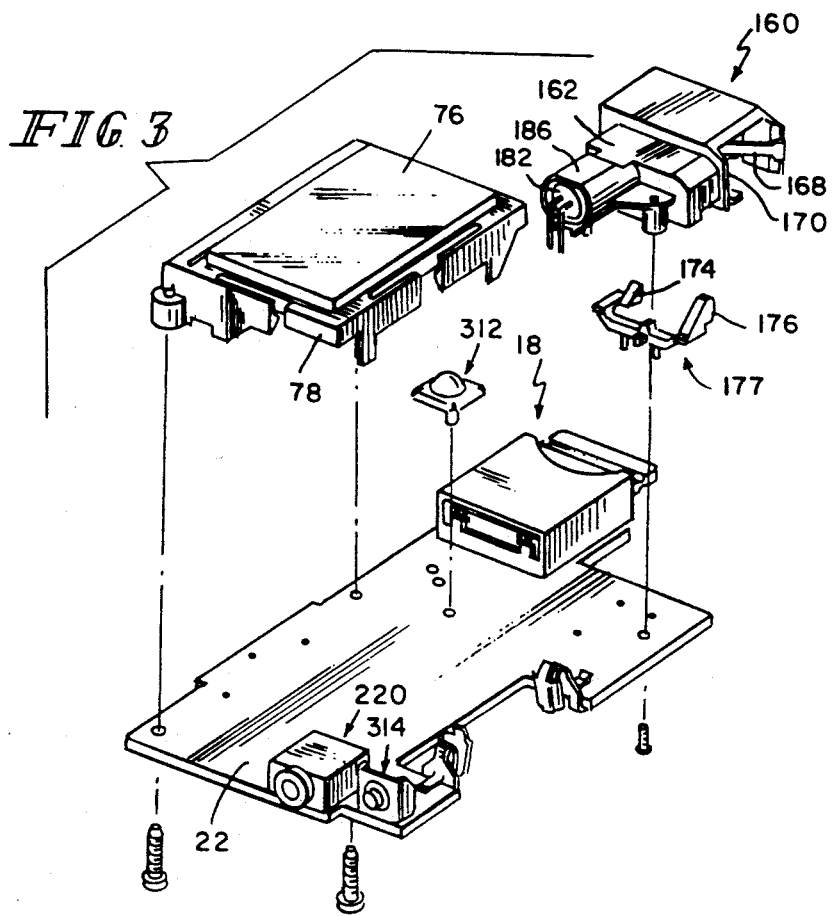

The front and rear portions 14, 16 include respective, cooperating, somewhat arcuate cutouts 60, 62 (FIGS. 1, 6 and 8), for key housing portion 18. Key housing portion 18 is designed to receive an electronically readable information carrier, or key, 64 FIG. 2) of the type described in U.S. Pat. No. 5,053,199. The disclosure of U.S. Pat. No. 5,053,199 is incorporated herein by reference. Front and rear portions 14, 16 also include cooperating cutouts 68, 70 (FIGS. 1, 6 and 8) for receiving the strip carrier holder portion 20. Front portion 14 also includes a window 74 (FIGS. 1 and 8) around which a liquid crystal display 76-supporting bezel 78 (FIGS. 3 and 7) fits on the inside of front portion 14. Bezel 78 mounts the LCD 76 so as to be visible through window 74 and provides the necessary electrical connections 79 to LCD 76.

The back portion 16 of the case 12 also includes means for mounting a piezoelectric beeper transducer 80 (FIG. 6) and for providing electrical contact 81 thereto and a battery housing cutout 82 having a pivotally mounted door 84 for convenient insertion and removal of a six-volt battery 86.

The lips 88, 90 of front and back portions 14, 16, respectively, are complementarily configured to snap together. As further insurance against their inadvertently coming apart, a self tapping screw 92 (FIG. 1) through back portion 16 and into a stem 94 molded on the inside of front portion 14 holds portions 14, 16 together. Screw 92 extends through a hole 96 provided therefor in printed circuit board 22, which, along with the configurations of the interiors of front and back portions 14, 16, holds board 22 in place.

Figure 4:
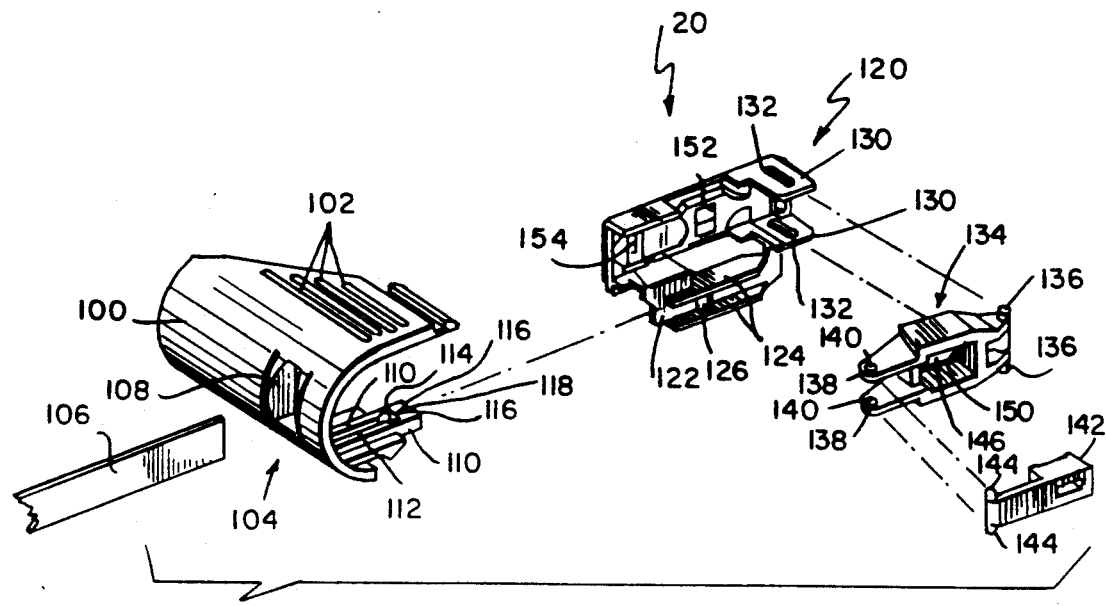

The strip carrier holder portion 20 includes an outer case portion 100 provided with grooves 102 (FIG. 4) on its top and bottom surfaces to aid in gripping it and snapping it into and out of engagement with the front 14 and back 16 case portions. Case portion 100 is provided with an opening 104 for inserting chemistry strips 106, the remissions of which are to be read, into the instrument 10. The margins 108 of opening 104 are somewhat funnel-shaped to assist in insertion of the strips 106 into the instrument 10 in the correct orientation. A pair of somewhat pawl-shaped members 110 extend rearwardly of case portion 100 beneath opening 104. Members 110 define between them a slot 112 which opens into a somewhat equilateral triangular region 114 near their remote ends 116, then closes back to its slot configuration, and then opens into a somewhat funnel shape 118 adjacent the remote ends 116 of members 110. A strip carrier body 120 includes a lower web portion 122 along each of the opposite sides of which extend two guide ribs 124. Web portion 122 is only slightly thinner than slot 112 is for most of its length. Guide ribs 124 are spaced apart only slightly further than the vertical thickness of each of members 110. These dimensions permit strip carrier body 120 to be slid into the slot 112 defined between members 110. A triangular horizontal cross section projection 126 spaced an appropriate distance along web portion 122 on each side thereof between guide ribs 124 cooperates with region 114 on case portion 100 to lock strip carrier body 120 between members 110.

Near its end remote from case portion 100, strip carrier body 120 includes a pair of horizontally projecting ears 130, each of which is provided with an elongated slot 132. Slots 132 extend generally transversely to the directions of motion of strips 106 as the strips are inserted into opening 104 and into the strip carrier holder 20 and removed therefrom. A lift 134 includes a pair of vertically, oppositely extending trunnions 136 which engage in respective slots 132 to permit lift 134 to move away from strip carrier body 120 as a strip 106 to be read is inserted therebetween. Lift 134, in turn, includes a pair or horizontally extending ears 138 at its forward end opposite the end at which trunnions 136 are provided. Each ear 138 is provided with a vertically extending circular cross section hole 140. A high reflectance (remission) white tile 142 is provided with a pair of trunnions 144 by which it is pivotally attached, by insertion of trunnions 144 into respective holes 140, to lift 134. Directly across from the point 146 at which white tile 142 projects through an opening 150 provided therefor in lift 134, strip carrier body 120 is provided with a slot 152. Strip carrier body 120 is also provided with another slot 154 between slot 152 and case portion 100, and with a frustoconical relief 156 (illustrated only in FIG. 1) on the side thereof opposite the side to which lift 134 is attached.

Figure 5:
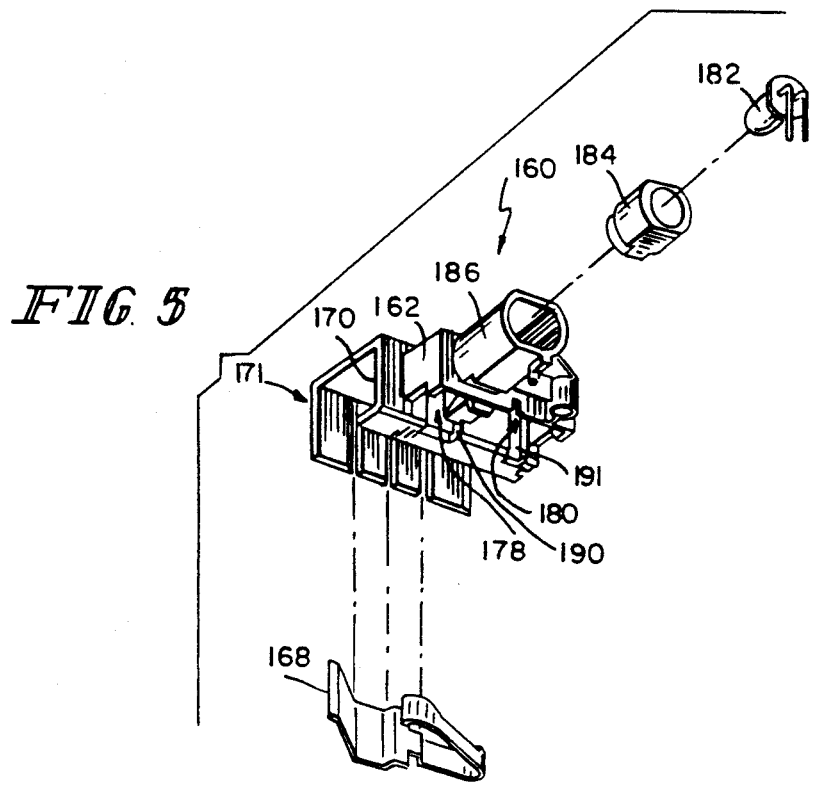

An optics assembly 160 (FIGS. 1, 3 and 5) mounted on the printed circuit board 22 cooperates with the strip carrier holder portion 20. The cooperation of these two components negates any possible misalignment errors between the optics and the strips 106. This cooperation is aided by the designs and tolerances of some of the molded plastics parts from which the strip carrier holder portion 20 and optics assembly 160 are largely constructed. These designs and tolerances permit the components of the strip carrier holder portion 20 and optics assembly 160 which must be properly aligned for accurate reading of the reacted strips' 106s' remissions to align properly when the strip carrier holder portion 20 is assembled into the instrument case 12.

Optics assembly 160 includes an optics housing 162. Housing 162 houses a leaf spring 168 and, across from spring 168, a wall 170 against which the spring 168 forces the strip carrier body 120 to position it and its related components 134, 142 and a strip 106 carried thereby properly relative to the instrument 10's optics. A frustoconical projection (not illustrated) projecting toward spring 168 from wall 170 adjacent the inner end 171 of housing 162 engages relief 156 on strip carrier body 120 when strip carrier body 120 is correctly positioned in optics housing 162. A pair 174, 176 (FIG. 3) of transparent plastic prisms, molded as a single piece 177, are mounted on printed circuit board 22 in separate internal regions 178, 180, respectively, (FIG. 5) of housing 162. A light emitting diode 182 is mounted on board 22 and fitted into an LED adapter 184 which, in turn, is fitted into an LED socket 186 provided on housing 162. LED 182 is the initiation, or "upstream" end, of a glucose measurement channel.

Wall 170 is provided with a vertical slit opening 190 opposite the opening of socket 186 into housing 162. In the assembled optics assembly 160, this slit opening 190 is directly adjacent prism 174, the smaller of the two prisms provided by piece 177. In order to avoid receiving the direct reflected light from the reacted test chemistry on a strip 106, prism 174 is oriented at an angle to the surface of the strip 106 other than the angle of incidence of light from LED 182 onto, or the angle of reflection of light from LED 182 from, strip 106. Illustratively, prism 174 is oriented at an angle of about 77° to the surface of strip 106. This increases the likelihood that light received by prism 174 is not direct reflected light, but rather ambient remission light, from the reacted chemistry on strip 106. This diffuse light is a better gauge than direct reflected light of the end point of the reaction between the glucose in blood applied to strip 106 and the chemistry with which strip 106 is treated. Thus, this ambient remission light is a better gauge of the concentration of the glucose content of the blood.

Prism 176 is oriented directly adjacent a slit opening 191 through wall 170 in the assembled optics assembly 160. The problem of obtaining a diffuse or remission light component of the light reflected from strip 106 is not so great with the light entering prism 176 as it is with the light entering prism 174 because the light entering prism 176 is used only to determine whether there is a strip in strip carrier body 120, and, if so, whether the strip is properly oriented with its chemistry immediately opposite opening 190 and prism 174. Since prism 176 is not in the chemistry reading channel 164, the remission reading from it is not so critical.

Both of prisms 174, 176 have curved faces facing strip 106. These curved faces function as lenses to focus the light remissions entering the prisms on the devices which detect these remissions. The lenses incorporated into prisms 174, 176, in other words, have focal lengths equal to the distances from the lenses to their respective regions of interest on the strip 106 and also equal to the distances from the lenses to their respective detector devices.

Turning now to FIG. 9, the operation of instrument 10 is controlled by a microcomputer ($\mu$c) 200 such as the NEC type $\mu$PD75P308 $\mu$c. All subsequent references herein to pin and terminal numbers and names will be to the pin and terminal numbers and names of the specific integrated circuits and other devices identified herein as exemplary. It is to be understood, however, that other integrated circuits may exist which are equally suited to provide the functions required by instrument 10. The clock for $\mu$c 200 is a 4.19 MHz Crystal 202 which is Coupled across terminals X1-X2 thereof. The terminals of crystal 202 are also coupled through respective 33pF capacitors to ground. The $V_{DD}$ supply for $\mu$c 200 is provided by a PNP transistor 204 such as a BC858C, the base of which is coupled through a 62K$\Omega$ resistor 206 to terminal P4.1 of $\mu$c 200. The collector of transistor 204 is coupled to positive battery voltage (+6VDC), hereinafter referred to as VBAT. $V_{DD}$ appears at the collector of transistor 204. The collector of transistor 204 is coupled to its emitter by the parallel combination of two 200 $\Omega$ resistors. The cathode of a diode 208 is coupled to the collector of transistor 204. The anode of diode 208 is coupled to ground. Diode 208 illustratively is a type 1N4148 diode.

The RESET terminal of $\mu$c 200 is coupled to the collector of a transistor 210 and through a 10K $\Omega$ resistor to $V_{DD}$. The emitter of transistor 210 is grounded. Its base is coupled through a 22K$\Omega$ resistor 212 to the junction of a 0.1 $\mu$F capacitor 214 and a 1M$\Omega$ resistor 216. The other terminal of capacitor 214 is coupled to VBAT. The other terminal of resistor 216 is coupled to ground.

An electronic log book mode (ELB) connector 220 has three terminals. A first of these, 222, is coupled through a 10K$\Omega$ resistor to terminals P 3.0/LCDCL and P 0.0/INT4 of $\mu$c 200. Terminal 222 is also coupled to ground through the parallel combination of a 680pF capacitor and a 220K$\Omega$ resistor. Terminal 224 is coupled through a 10K$\Omega$ resistor to terminal P3.2 of $\mu$c 200, and to ground through the parallel combination of a 680pF capacitor and a 220K$\Omega$ resistor. Terminal 226 is coupled to ground.

The eight terminals 231-238 of the key housing portion 18 are coupled, respectively, to: $\mu$c 200's terminal P7.3/KR7; $\mu$c 200's terminal P7.2/KR6; $\mu$c 200's P7.0/KR4; $\mu$c 200's terminal P6.3/KR3; ground; one terminal of a 220K$\Omega$ resistor 240, the remaining terminal of which is coupled to terminal 234; nothing (blank); and terminal 236.

A number of variables exist which affect the reading of the reacted chemistry on a strip 106. For the reading to be as free of errors as instrument 10 can make it, these variables must be accounted for to the extent possible by instrument 10 in the process of calculating the end point remission of the reacted chemistry. One of these variables is humidity, and it is taken into consideration by a humidity sensor 242 of standard configuration coupled between ground and an input terminal P0.3/SI/SB1 of $\mu$c 200. Humidity sensor 242 is also coupled through a 1M$\Omega$ resistor 244 and a 0.01 $\mu$F capacitor 246 to ground. VBAT is supplied to the emitter of a PNP transistor 248, illustratively a BC858C. The collector of transistor 248 is coupled to key housing portion 18's connectors 236 and 238 and to the junction of resistor 244 and capacitor 246.

An internal EEPROM 250 has its CS, SK, DI and DO terminals coupled, respectively, to the P7.1/KR5, P7.2/KR6, P7.0/KR4 and P6.3/KR3 terminals of $\mu$c 200. The $V_{CC}$ and ORG terminals of internal EEPROM 250 are coupled to the collector of transistor 248. The GND terminal of internal EEPROM 250 is coupled to ground. Internal EEPROM 250 illustratively is a Catalyst Semiconductor type CAT93C46 integrated circuit, as is the integrated circuit in code ROM key 64.

A series string of an 8.2K$\Omega$ resistor 252, a 10K$\Omega$ resistor 254, a 10K$\Omega$ resistor 256, and a 10K$\Omega$ resistor 258 is coupled between terminal P6.1/KR2 of $\mu$c200 and ground. The junction of resistors 252, 254 is coupled to terminals VLC0 and BIAS of $\mu$c 200. The junction of resistors 254 and 256 is coupled to terminal VLC1 of $\mu$c 200. The junction of resistors 256 and 258 is coupled to terminal VLC2 of $\mu$c 200.

Transducer 80 is coupled across terminal P2.3/BUZ of $\mu$c 200 and ground. A diode 260 is coupled across transducer 80 with its anode coupled to ground and its cathode coupled to terminal P2.3/BUZ. Another diode 262 has its anode coupled to terminal P2.3/BUZ and its cathode coupled to $V_{DD}$.

The COM0-COM2 and DS10-DS0 terminals, respectively, of $\mu$c 200 are coupled to respective terminals of the same names, pins 1-14, of LCD 76.

An infrared strip 106 sensor channel 166 includes an LED 264 and a light sensitive transistor (LST) 266 separated by a partition in a common housing (not shown). The larger prism 176 is mounted on printed circuit board 22 so that its bottom surface rests directly on the top surface of the housing in which LED 264 and LST 266 are housed. LED 264 and LST 266 illustratively are a Toshiba type TLP908 integrated circuit. Light from LED 264 shines upward through the bottom of the larger prism 176 and is reflected out through the lens of prism 176 onto the strip 106. The reflected light returns through the lens and is reflected downward within the prism 176 and out the bottom thereof where it is received by LST 266. The resultant conductivity of LST 266 corresponds to a certain percentage remission of the light from LED 264. That percentage remission establishes whether a strip 106 is present in strip carrier body 120 and, to an extent, whether that strip 106, if present, is properly oriented.

The way the strip 106 and strip 106 orientation are detected is as follows. Light returning in channel 166 to the base of LST 266 causes it to conduct. A current mirror including NPN transistors 268 and 270 in conventional current mirror configuration provides equal currents through the collectors of these two transistors in response to current flow in the emitter of LST 266. A 0.47 μF capacitor 272 is coupled across the collector and emitter of transistor 270 and discharges at a rate determined by the amount of light falling on the base of LST 266 to which LST 266 is sensitive. This configuration subtracts from the initial voltage across capacitor 272 the integral of the light falling on the base of LST 266. Current is supplied to LED 264 for a predetermined, set period of time. The remission from strip 106 to the base of LST 266 determines how deeply discharged capacitor 272 becomes. Capacitor 272 is then charged from a constant current source for a period of time which is measured using the system clock, until capacitor 272 has recharged to some reference voltage. The length of the period that capacitor 272 takes to recharge to reference voltage is a period of time, a number of strokes of the system clock, and converts to a digital value the percentage remission of channel 166. This translates into the presence or absence of a strip 106 in the strip carrier body 120 and, to an extent, its orientation in strip carrier body 120. The instrument 10, once it has established that a strip 16 is present in the strip carrier body, next decides whether the strip 106 is properly oriented with its reagent pad in front of slot 190 and prism 174, or whether the strip 106 is backward or upside down. Of course, the strip architecture must be such that different ranges of percentage remission readings are presented for these different strip 106 orientations, and this is so. See U.S. Ser. No. 07/661,788.

To accomplish these objectives, the anode of LED 264 is coupled to VBAT and its cathode is coupled to the collector of a transistor 276, which illustratively is a type BC848C NPN transistor. The emitter of transistor 276 is coupled through an 82Ω feedback resistor to ground. The base of transistor 276 is provided with periodic LED 264 drive signals from terminal P5.1 of μc 200. The base of transistor 276 is also coupled through two diode-connected temperature compensation transistors 280, 282 in series to ground. Transistors 268, 270, 280, 282 illustratively are a type MC3346D quad transistor integrated circuit. The emitter of LST 266 is coupled to the collector and base of current mirror transistor 268, and to the base of current mirror transistor 270. The collector and base of transistor 268 and the base of transistor 270 are also coupled to terminal P5.0 of μc 200. The emitters of transistors 268, 270 are grounded. The collector of transistor 270, in addition to being coupled to capacitor 272, is coupled to the inverting (−) input terminal of a difference amplifier 286, and to the collector of a PNP transistor 288 such as a type BC858C transistor. The output terminal of difference amplifier 286 is coupled to the P3.1/SYNC terminal of μc 200. The emitter of transistor 288 is coupled to terminal P5.3 of μc 200. The base of transistor 288 is coupled to the output terminal of a difference amplifier 290.

The inverting (−) and non-inverting (+) input terminals of difference amplifier 290 are coupled through a 20KΩ resistor and a 150Ω resistor, respectively, to the collector of LST 266. A 5.1KΩ resistor is coupled from the base of transistor 276 to the collector of LST 266 as well. The collector of LST 266 is coupled to the + input terminal of a difference amplifier 294, the − input terminal of which is coupled through a 150KΩ resistor to terminal P6.0/KRO of μc 200. The output terminal of difference amplifier 294 is coupled to terminal P3.3 of μc 200. The − input terminal of difference amplifier 294 is also coupled through a 0.01 μF capacitor to ground.

Turning now to the mechanism and electronics by which the remission of the reagent pad portion of strip 106 is read when a strip 106 is properly inserted into strip carrier body 120, LED 182 is the beginning of channel 164. The anode of LED 182 is Coupled to VBAT and its cathode is coupled to the collector of an NPN transistor 298. Transistor 298 illustratively is a type BC848C transistor. The emitter of transistor 298 is coupled through a 120Ω feedback resistor to ground. The base of transistor 298 is coupled to terminal P5.2 of μc 200, and through a 20KΩ resistor to the + input terminal of difference amplifier 294. The remission of the reagent pad of a strip 106 is supplied to a photosensor 300, such as a Siemens type TFA1001W integrated photosensor. Photosensor 300 is mounted in closely spaced relation to the bottom of the smaller prism 174 so that remissions from the chemistry region of strip 106 that enter the lens surface of prism 174 are reflected down through it and exit from its bottom into photosensor 300.

Power for photosensor 300 is provided through a PNP transistor 302, which illustratively is a type BC858C transistor. The emitter of transistor 302 is coupled to VBAT. Its base is coupled through a 62KΩ resistor to terminal P4.2 of μc 200. Its collector is coupled to ground through a 22 μF tantalum capacitor 304. The voltage VD1 across capacitor 304 is coupled across terminals + VS and − VS of photosensor 300. A 0.01 μF capacitor is also coupled across terminals + VS and − VS. The VSTAB and FCOMP terminals of photosensor 300 are joined through a 1MΩ resistor. The VSTAB terminal is also coupled to the + input terminal of a difference amplifier 308. The − input terminal of difference amplifier 308 is coupled to its output terminal, making it an inverting amplifier. The output terminal of difference amplifier 308 is also coupled to the + input terminal of difference amplifier 294. Difference amplifiers 286, 290, 294 and 308 illustratively are a type LM324A quad difference amplifier integrated circuit.

Terminal P6.2/KR2 is coupled through a 220KΩ resistor to the anode of a diode 310 which illustratively is a type IN4148. The cathode of diode 310 is coupled to the INHIBIT terminal of photosensor 300. The conductor extending between the cathode of diode 310 and the INHIBIT terminal of photosensor 300 is capacitively coupled through a 680Ω resistor to ground and through a 360Ω resistor to the + input terminal of difference amplifier 286. The + input terminal of difference amplifier 286 is coupled through a 200Ω resistor to the + input terminal of difference amplifier 290. The OUTPUT terminal of photosensor 300 is coupled to the − input terminal of difference amplifier 286.

One terminal of an ON/OFF switch 312 operated by ON/OFF button 32 is coupled to ground. The other terminal of ON/OFF switch 312 is coupled to the P1.1/INT1 terminal of μc 200. The P1.2/INT2 terminal of μc 200 is coupled to one terminal 316 of a memory switch 314 operated by memory button 50. Terminal 316 of memory switch 314 is coupled through a 220KΩ resistor to ground. The other terminal of memory switch 314 is coupled through a 220KΩ resistor to the P1.1/INT1 terminal of μc 200.

The symbols which can appear on LCD 76 include numbers 00.0 through 99.9, the indications mg/dL (milligrams per deciliter), mmol/L (millimoles per liter), mem (which stands for memory), a battery icon, an icon of a blood droplet being deposited on a strip, the word code, and an error icon, a box with an "X" through it, each quadrant of the box being capable of being separately energized.

Figure 10:
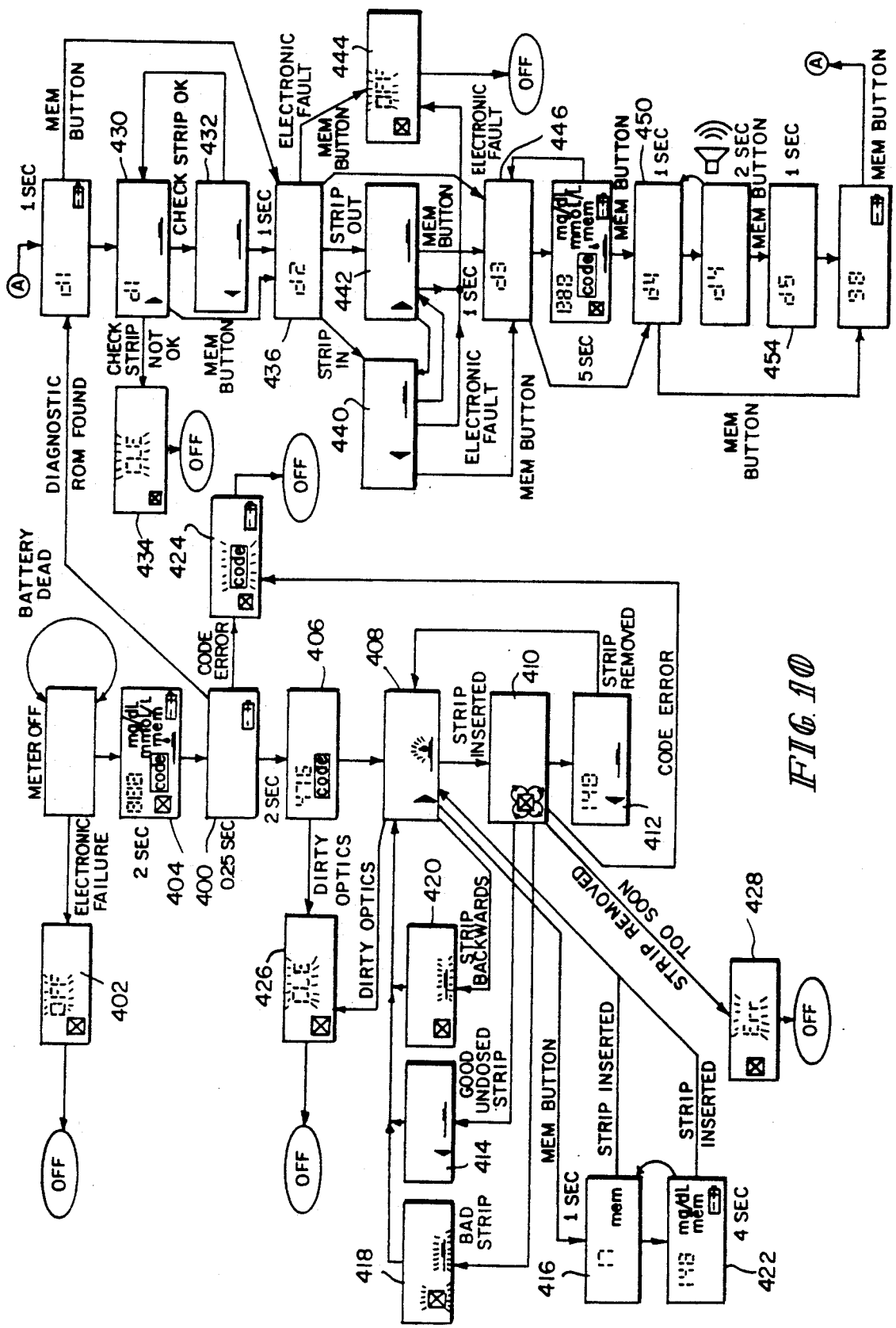
FIG. 10 illustrates a type of flow diagram useful in understanding the operation of the instrument illustrated in FIGS. 1-8.

Referring now to FIG. 10, the instrument 10 is turned on by depressing ON/OFF button 32. Instrument 10 actuates prior to release of ON/OFF button 32. Immediately after the instrument 10 is turned on, it performs 400 a power-on system integrity test and a battery voltage test. If the battery 86 voltage is below 4.5 volts, a battery low warning (battery icon on LCD 76) is displayed. If the battery 86 voltage is below 4.2 volts, the instrument 10 will not turn on 402. Following being turned on, all segments of the display 76, including all icons, are displayed 404 for 2 seconds. If it is enabled, the transducer 80 sounds for the first one/half second of this 2 second display check.

After 2 seconds, all segments and icons disappear and the ROM code number from key 64 and code icon appear 406 on LCD 76 for 2 seconds, then disappear. During this time, the instrument 10 scales itself using the remission of white tile 142. Scaling is followed by the lighting 408 of the strip icon, right arrow icon, and flashing blood drop icon. This icon display prompts the user to apply blood to the strip 106 and then to insert the dosed strip 106 into the opening 104 provided therefor in instrument 10.

The user applies blood to the strip 106 and allows it to soak into the strip mesh until it is fully absorbed. Within two seconds of proper insertion of the strip 106, the instrument 10 deletes the strip icon, blood drop icon and right arrow icon from display 76, and begins the timing period for the chemistry in the reagent pad of strip 106 to react with the medically significant component, glucose in this example, of the applied blood. Within two seconds of insertion of the strip 106, the display 76 sequentially displays 410 (in clockwise rotation) the quadrants on the error or "X" display at a rate of one segment per half second. No timing need be displayed on the instrument 10's LCD 76 because of the employment of an endpoint chemistry on strips 106. When the strip 106's reaction is determined by the instrument 10 to have reached an endpoint, the instrument 10 beeps once and then displays 412 a blood glucose value and the mg/dL icon. The instrument 10 also displays the strip icon and left arrow icon to prompt the user to remove the reacted strip 106. The glucose result is stored in the newest (first) memory location, pushing all previously stored glucose readings down one location in memory.

After the strip 106 is removed, the instrument 10 again rescales itself from the white tile 142 to ready itself for the next strip 106 reading. The instrument 10 then returns to the dosed strip insertion prompt 408.

The instrument 10 can verify that an unreacted strip 106 is acceptable for use. It does this by reading the unreacted strip 106 to make sure that its reagent pad remission value is within the specified percent remission limits stored in the code ROM key 64. Performance of this check is at the user's discretion. The instrument 10 is capable of performing 410, 414 this check when the instrument is prompting 408 for a dosed strip or during 408, 416, 408, 410, 414 a memory recall display.

To perform this strip 106 integrity check, the user removes an unreacted strip 106 from the vial containing such strips and inserts the unreacted strip 106 into the instrument 10's slot 104 with the reagent pad facing the optics. Within two seconds after a strip 106 has been inserted, the instrument 10 detects the presence of a strip 106 and begins 410 its timing display. During this display, the user must depress 416 the memory button 50 once. This causes the instrument 10 to perform the strip 106 integrity check. After the memory button 50 has been pressed, the instrument 10 will read the strip 106's remission and compare the strip 106's remission against the programmed limits that have been provided by the lot specific ROM key 64.

Strip 106 integrity approval is signaled through the strip removal prompt 414 and a single beep. Strip 106 approval permits the user to proceed with a test on a reacted strip 106 by prompting 408 for a dosed strip after the unreacted strip 106 is removed.

Strip integrity errors are signaled 418, 420 through the display of the flashing error ("X") icon, flashing strip icon and three beeps. The instrument 10 remains in this display state until the bad strip 106 is removed. After strip 106's removal, the instrument 10 prompts 408 for a dosed strip.

Glucose test values are stored automatically after every test using "first (oldest) in, first deleted" and "last (newest) in, first recalled" protocols. Once the memory has filled to its thirty reading capacity, each new reading added causes the oldest reading to be deleted from memory.

Memory recall mode 416 is accessible from the dosed strip prompt 408. Memory recall function is initiated by pushing the memory button 50 once. This displays the first memory location (1).

After one second, the display changes 422 to display the contents (a glucose reading) of the selected memory location. The display reverts 416 to the memory location display (1 in this example) after 4 seconds. If no button is pushed, the cycle of memory location 416 and memory location contents 422 continues to repeat itself for 5 minutes before the instrument 10 turns itself off. The memory display cycle can also be terminated by the insertion 416, 422, 408 of a test strip 106 into the instrument 10. Recall of the remaining values from memory is accomplished by pressing 408, 416 the memory button 50 over and over again until all thirty stored values and their memory locations have been displayed. Each time the memory button 50 is depressed, the next memory location is displayed. Memory locations and results cycle to location 1 once the user advances beyond the oldest value. If fewer than 30 results are stored in memory, the first location (location 1) is displayed following the last result stored when the memory is advanced beyond the last result. The memory icon is displayed 416, 422 at all times during memory recall.

If at any point 416, 422 a strip 106 is inserted, the instrument 10 reverts 408, 410 to the test/timing mode. Insertion of a strip 106 (reacted or unreacted) automatically causes the instrument 10 to revert to this mode and resets memory to the first (newest) location.

The instrument 10 uses the code ROM key 64 as follows: With the instrument 10 off, the user removes the old ROM key 64 from the instrument 10 and discards it. A new ROM key 64 is packaged in every supply of strips 106. The user inserts the new ROM key 64 containing information pertinent to the new supply of strips 106 into the key housing portion 18 on the instrument 10 prior to turning the instrument 10 on. When the instrument 10 is turned on, the instrument 10 checks the integrity of the data contained in ROM key 64 via a checksum method. If the ROM key 64 data is found to be questionable, then a code error is displayed 424.

During the performance 410 of a test, prior to the calculation 412 of a new glucose result, the instrument 10 checks the ROM key 64 to see if it has been changed. If the ROM key 64 has been changed since the instrument 10 was turned on, a code error is displayed 424. The instrument 10 remains in this display until it either times itself off (5 minutes), or is turned off.

When test results exceed the upper limit contained in the ROM key 64, then the message HI is displayed in place of a numeric result. If the result does not exceed the lower limit contained in the ROM key 64, LO appears on the display. The mg/dL icon is displayed in both cases.

Instrument 10 verifies the remission of its white tile 142 and signifies a dirty tile 142 by displaying 426 CLE (for "clean") on display 76. The instrument 10 does not permit the user to begin a testing procedure or memory recall from this display. The only remedy for this error is to turn the instrument 10 off. This error occurs if the slope calculated 406 from the remission of the white tile 142 is not within instrument 10's internal slope limits, typically +5% to −10% of its target value. This error also occurs 408 if the instrument 10 is turned on with a strip 106 inserted in it.

The instrument 10 shuts itself off automatically 5 minutes after the last button push or strip 106 insertion. Automatic shut off occurs regardless of instrument 10 mode or the last button pressed. Depressing ON/OFF button 32 while the instrument 10 is on turns the instrument 10 off.

Transducer 80 provides an audible beep: when the instrument 10 is turned on (0.5 second); when a strip 106 is inserted into opening 104 (0.25 second); whenever an error message is displayed (three times for 0.1 second each); at the end of a test to indicate that a result is displayed or an unreacted strip 106 is usable (0.25 second): and, whenever either button 32 or button 50 is depressed as a "key click" sound (two cycle duration). Transducer 80 actuation can be enabled/disabled by the simultaneous actuation of both ON/OFF button 32 and memory button 50 as the instrument 10 is turned on.

The instrument 10 denotes errors by displaying 428 the "X" icon in combination with an error message or other icon. There are two error types: recoverable and non-recoverable. Strip errors are correctable by removal of the strip 106 from the instrument 10. All other errors are non-recoverable and require the instrument 10 to be turned off in order to clear the error.

The following errors are recoverable strip errors. Removal of the strip will cause the instrument 10 to return to the dosed strip prompt 408: the Bad Strip error 418, caused by an improperly reacted strip 106 or a strip 106 which is degraded in any way as to make its state indeterminable; and the Strip in Backwards error 420, caused by the strip 106 being inserted with its blood application side toward the instrument 10's optics.

The following errors are non-recoverable, as they are the results of instrument measurement problems: the Dirty Optics error 426, which occurs if the instrument 10's white tile 142 is dirty or degraded, or if the instrument 10 is turned on with a strip 106 already inserted in it; the Electronics Fault error 402, which is caused by the detection of a fault during the instrument 10's power-on self-test or during a diagnostic check; the Strip Removed During Test error 428, which is caused by removing a strip 106 during the performance of a test so that instrument 10 is unable to complete the test cycle; and, the Coding error 424, which is caused by the detection of a code ROM key 64 read error or a mismatch of the lot code number read when instrument 10 is turned on with the lot code number read just prior to the calculation of a glucose result. The only remedy for these errors is to turn the instrument 10 off.

The instrument 10 provides certain prompt messages to the user, including: the Strip Removal prompt, by which the instrument prompts the user to remove a strip 106 by displaying the strip icon and left arrow (<) icon; and the Dosed Strip prompt, by which the instrument 10 prompts the user to insert a dosed strip 106 by displaying the strip icon, right arrow (>) icon, and flashing the blood drop icon. Flashing segments or icons in any mode of operation are displayed for 0.5 second and off for 0.5 second.

In addition to its normal operating mode for determining the remissions of reacted test strips, the instrument 10 has a diagnostic software package that is accessed via installation of a special diagnostic ROM code key 64. The diagnostic ROM code key 64 is installed in key housing portion 18 before the instrument 10 is turned on. Once the instrument 10 is turned on with the diagnostic ROM code key installed, the following functions are accessible instead of the normal operating modes.

Once instrument 10 is turned on in the diagnostic mode, instrument 10 enters the check strip diagnostic 430. The instrument displays d1 in the glucose value field, or results field, for one second. After one second the instrument 10 additionally displays the strip icon and right arrow icon to prompt the operator to insert a check strip 106 provided with the diagnostic code ROM key 64. If the user presses memory button 50 during this display, the instrument 10 advances to the next diagnostic test 436.

Upon insertion 430 of the check strip, the instrument 10 measures the remission of the check strip and compares this remission to a target remission value range stored in the diagnostic code ROM key 64. If the measured remission agrees with the target value range then the results field of the display 76 is blank, transducer 80 beeps once and the user is then prompted 432 to remove the check strip by turning off the right arrow icon, and turning on the left arrow icon while continuing to display the strip icon.

Upon removal of the check strip from the instrument 10 after a successful check, the instrument 10 returns 430 to the start of the check strip diagnostic routine and remains in this routine until the instrument 10 is turned off, or until the user advances to the next diagnostic routine by pressing the memory button 50.

If the measured remission of the check strip does not match 434 the target value in the diagnostic code ROM key 64, the instrument 10 beeps three times, CLE flashes in the results field on display 76, and the error icon "X" is displayed. The only way to exit this display is to turn instrument 10 off.

If the user advances past the first diagnostic check 430 by pressing memory button 50, then the IR (infrared) sensor check is prompted 436 by displaying d2 in the results field. After one second, the instrument 10 checks for the presence of a strip in the instrument by using the reagent pad detector. If the instrument 10 determines 440 that a strip 106 is in the instrument 10, it prompts the user to remove the strip by displaying the strip icon and left arrow icon until the strip is removed.

If the instrument 10 detects 442 no strip, the instrument 10 then reads the IR detector 266. If the IR detector 266 reads a remission value inconsistent with an empty strip carrier 120, 134, then instrument 10 displays OFF 444 in the results field of display 76 to signify that the IR detector 266 is sensing a strip 106 when none is present. This display will remain until the instrument 10 is turned off.

If the instrument 10 determines 436, 442 that no strip 106 is present and that the IR detector 266 sees no strip 106, then it prompts 442 the user to insert a strip 106 by displaying the strip icon and right arrow icon until a strip 106 is detected by the reagent pad detector 300. Once a strip 106 is sensed by the reagent pad detector 300, the strip detector 266 is measured. If this measurement is inconsistent with the presence of a strip 106 in the instrument 10, then the instrument 10 beeps three times, the display field displays OFF 442, 444 and the error X icon flashing until instrument 10 is turned off.

If the IR detector 266 senses 436, 440 the presence of a strip 106 in the instrument 10, then the results field of display 76 is blank, and the user is prompted 440 to remove the strip 106 by displaying of the strip icon and left arrow icon. Once the strip 106 is removed, the display 76 returns to the d2 display until the user advances to the next diagnostic check 446 by pressing memory button 50 or until instrument 10 is turned off.

If the user advances past the customer control strip diagnostic 430 and past the IR sensor 266 check 436 by using memory button 50, then the display check 446 will be prompted by displaying d3 in the results field for one second. After one second, all segments of the display 76 will be displayed for five seconds. Display 76 then alternates between the d3 display and the all segments display until the user advances to the next diagnostic check 450 by pressing memory button 50 or until instrument 10 is turned off.

If the user advances past the first three diagnostic checks 430, 436, 446 by using memory button 50, then the d4 prompt for the transducer 80 check 450 will be displayed in the results field. After one second, transducer 80 beeps for two seconds regardless of whether the user has transducer 80 switched off or not. After transducer 80 has beeped for two seconds, it will turn off for one second and then on for two seconds and so on, until the user advances to the next diagnostic check 454 by pressing memory button 50 or until the instrument 10 is turned off.

If the user advances past the first four diagnostic checks 430, 436, 446, 450 using memory button 50, then instrument 10 enters the battery check 454 and prompts the user by displaying d5 in the results field, and displaying the battery icon. At the end of one second, the instrument 10 repeats its power-on battery check 400.

The instrument 10 displays a number based on the following calculation:

$$\frac{\text{present battery voltage}}{\text{battery low warning voltage}} \times 100$$

Of course, numbers of less than 100 are displayed if the battery icon was being displayed prior to entering 454 the d5 diagnostic.

This display will remain on until the user returns a to the first diagnostic check, d1, by pressing memory button 50 or until instrument 10 is turned off.

The operation of certain software functions of the disclosed instrument may be better understood by reference to the attached source listing for $\mu$C 200 and illustrative data stored in the EEPROM of a typical key 64. In the source listing, CRD or Chemistry Remission Difference is the amount of remission difference which a delta must be less than in order to reach the end of reaction (EOR). CRD is a 12 bit number in bank 1 RAM which is an input to the function REACTION. The format of CRD is a 12 bit binary remission multiplied by forty.

IWMI is an 8 bit number in bank 1 RAM which is an input to function REACTION which determines the number of half second increments of time to delay before taking the first remission. IWMI is allowed to be from 0 to 255. If IWMI equals 0, then no delay will occur. If it equals 1 then one half second of delay will occur, and so on.

TINC is an 8 bit number in bank 1 RAM. TINC is an input to the function REACTION which determines the number of half second increments of time which will elapse between successive remission readings. TINC is permitted to be from 0 to 255. If it is 0, then one half-second increment of time will elapse. If it is 1, then two half-second increments will elapse, and so on.

NPS is an input to the function REACTION which is a 4 bit number in bank 1 RAM. NPS represents the number of remission readings that will be taken between comparisons. It is allowed to be from 1 to 6. If NPS=1, then one remission reading is taken between those which are compared, and so on.

NPSA is an 8 bit number in bank 1 RAM which is an input to function REACTION. NPSA is a function of NPS. NPSA essentially contains the same information as NPS but in a form which is more easily used by the processor. It is defined as:

$$NPSA = (NPS + 1) * 8$$

IWMA is an 8 bit bank 1 RAM number. IWMA is an input to function REACTION. IWMA controls the number of comparisons that the EOR portion of the algorithm will make before it terminates. IWMA is permitted to be from 1 to 255. If IWMA equals 1, then only one comparison will be made. If IWMA equals 2, then a maximum of two will be made, and so on.

ERS is a 1 bit number in bank 1 RAM which is an input to function REACTION. ERS causes the MAX_F flag to be set if the function REACTION reaches EOR by reaching IWMA.

EORREM 1 is a 32 bit floating point number in bank 1 RAM which contains the last remission taken by function REACTION. EORREM 1 is an output of function REACTION.

EORCOUNT is an 8 bit bank 1 RAM number which contains the number of comparisons done during EOR. It will never equal 0. It will always be from 1 to 255. EORCOUNT is an output of function REACTION.

MAX_F is an output of function REACTION. MAX_F is a 1 bit bank 1 RAM number. MAX_F is set equal to 1 if EOR is reached by the number of comparisons equalling IWMA and ERS is also 1. If these conditions are not met, then MAX_F is cleared to zero.

TRACE_F is a 1 bit bank 0 (zero) RAM input to module REACTION which indicates that the meter is in TRACE MODE. In TRACE MODE, all remission readings are sent out the I/O port.

SE_F is a 1 bit bank 1 RAM number which is an output. If SE_F is set, a strip error has occurred. Two conditions can cause this: (1) EORREM 1 less than COL or greater than COH; or (2) EOR reached by finding a delta less than CRD, but the last 2 remissions taken did not have deltas less than CRD.

COL is a bank 1 RAM location. Its format is a 12 bit binary remission multiplied by 40. All EORREM 1 values found by this function are compared to this number. If EORREM 1 is less than COL, then SE_F is set.

COH is a bank 1 RAM location. The format is a 12 bit binary remission times 40. All EORREM 1 values found by this function are compared to this number. If EORREM 1 is greater than COH, then SE_F is set.

REACTION ASSESSMENT

Summary

Reaction Assessment is responsible for observing the strip adaptor and determining when the remission of the object in the strip adapter has reached the EOR. It does this by periodically taking full power chemistry pad remissions and analyzing these against parameters found in the external ROM. The final remission is placed in a reserved location in RAM. In addition, Reaction Assessment determines how many comparisons were made during the search for EOR. During the operation of this module, a rotating arrowhead is displayed on the LCD display as a means of indicating that this module is operating. This module also transmits the value of each remission taken out the serial port if TRACE_F is set. If the MEM button is pushed during the execution of this module, then control passes to the STRIP INTEGRITY module and Reaction Assessment is aborted.

More Detailed Explanation

This function is responsible for observing the strip adapter and determining when EOR occurs or if the MEM button is pushed. In addition, Reaction Assessment displays a rotating arrow on the LCD as a means of providing a visual indication that the meter is busy. It also outputs each remission taken if TRACE_F is set.

Reaction Assessment begins by clearing the LCD and darkening a single arrowhead. The first arrowhead darkened is not specified and will vary indeterminately. For the duration of the execution of this function the LCD will change its display every half second. The display will change by lightening the arrowhead that is currently dark and darkening the arrowhead which is adjacent to it in the clockwise direction. At the completion of this function the duration of time since the LCD display was changed will be between approximately 20 and 300 msec. A typical time will be around 100 msec. This duration varies with the time required to take a remission and whether TRACE_F is set or not. It is intended that if a continuation of the rotating arrowhead display is desired following the completion of this function, then it is necessary to wait another half second before changing the LCD display. In addition, SE_F is cleared at this time.

Reaction Assessment employs the power conservation module so that when it is not actively taking remission readings or doing calculations it puts the meter in a power conservation mode which minimizes power consumption yet still permits the meter to respond immediately to any event which can cause a termination of power savings.

Figure 11:
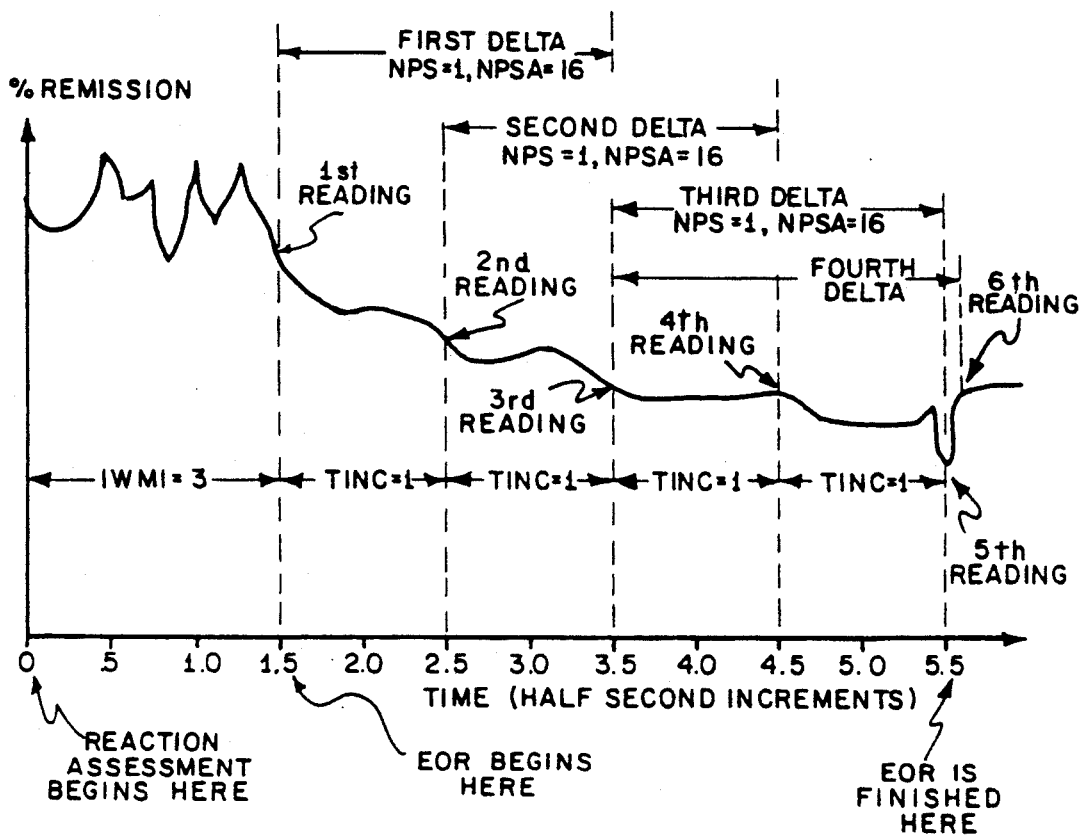
FIG. 11 illustrates a % remission versus time curve useful in understanding the operation of the software of the instrument of FIGS. 1-9.

The second thing that this function does is to examine RAM location IWMI to determine the amount of initial delay before taking the first remission reading. IWMI is an 8 bit binary integer. Each count of IWMI represents a half second of delay. IWMI may be from 0 to 255. 0 implies no delay and 255 implies 255 half seconds of delay. An example of IWMI is illustrated in FIG. 11. Here, IWMI has a value of 3. This causes 1.5 seconds of delay from the start of this function to where the first remission is taken.

Once the requirements of IWMI have been met, then a single, full power remission is taken on the chemistry channel. This remission is referred to as the first remission reading.

The next task that the function REACTION performs is a TRACE CHECK. This involves checking the 1 bit RAM location TRACE_F. If this location holds a 0, nothing happens. If it holds a 1, then the remission just taken is sent out the serial port as a 4 byte floating point number (least significant byte first) in the PC communication format.

The EOR portion of this function is conducted at this time. To reach EOR, one of two events must occur. Either a comparison of two remissions is found to have a change, or delta, which is less than CRD, or a timeout occurs after a number of comparisons equal to IWMA has been made.

End of Reaction by achieving a DELTA<CRD

CRD is a number found in RAM which is a limit for how small delta must be in order to constitute EOR. Delta is the result of subtracting the most recent remission from a prior remission determined by ROM code key 64 parameter NPS. The comparison between CRD and a delta is made as follows:

Is $|delta| < |CRD|$ ?

If the answer to this question is yes, then EOR has been reached. If not, then another comparison must be made.

The timing for these events can best be described in connection with FIG. 11. The first remission reading has already been taken (time=1.5 sec.). The amount of delay until a subsequent remission reading is taken is controlled by TINC. If TINC equals 0, then the delay increment will be one half second. If TINC equals 1, then 2 increments of one half second will occur. TINC is permitted to vary from 0 to 255, so it will provide delays of from 0.5 to 128 seconds. The example in FIG. 11 shows a TINC of 1 which causes a delay of two one half second increments between remission readings.

A delta is formed by comparing two remission readings. The two remissions compared are determined by RAM locations NPS and NPSA. NPSA=(NPS+1)*8. NPS refers to how many previous remissions will be skipped before using a remission to form a delta. If NPS equals 1, as in the example of FIG. 11, then one remission is skipped. For this example, the first delta is calculated after the third remission reading is taken. The delta is calculated by subtracting the first remission reading from the third remission reading. NPS is permitted to be from 0 to 6, permitting from 0 to 6 remission reading to be skipped between comparisons. If, for example, NPS=6, six remission readings are skipped, and the remission reading which was detected seven remission readings ago is the one that is used to calculate delta.

RAM location EORCOUNT is used to keep track of how many comparisons are made during this function. At the beginning of this function, EORCOUNT is set equal to zero. RAM location EORCOUNT is incremented by 1 each time a comparison is made until a delta less than CRD is found. If a delta is found that is less than CRD, then the software decides that EOR has been reached. In the example provided in FIG. 11, a delta less than CRD was reached when the fourth reading was taken. Therefore, the final EORCOUNT value for this example is 2.

Once the EOR is reached by finding a delta less than CRD, one more remission reading is taken after a time interval controlled by TINC. Following this remission, a Trace Check remission is read. This Trace Check remission is also compared to a previous remission controlled by NPSA. EORCOUNT is not incremented when this remission is read and its corresponding delta is calculated. If this delta is less than CRD, then the remission just taken will be stored at RAM location EORREM1. The software will then continue as described following the next paragraph. If this delta is not less than CRD, then the meter will continue as described in the next paragraph. FIG. 11 does not illustrate this condition since the fifth reading is quite low and the delta (THIRD DELTA) created thereby is greater than CRD. However, if THIRD DELTA had been less than CRD, then the fifth reading would have been the last and would illustrate this condition.

The meter next takes another remission reading immediately without waiting for TINC. This remission is compared to the same remission as is the remission taken after delta less than CRD. The example in FIG. 11 shows a delta being created between the third reading and the sixth reading. If the delta is not less than CRD, then the 1 bit RAM location SE_F is set. EORCOUNT is not incremented when this remission is read and its corresponding delta is calculated. This remission is stored at RAM location EORREM1. A Trace Check is performed. The function now proceeds as described below.

Figure 12:
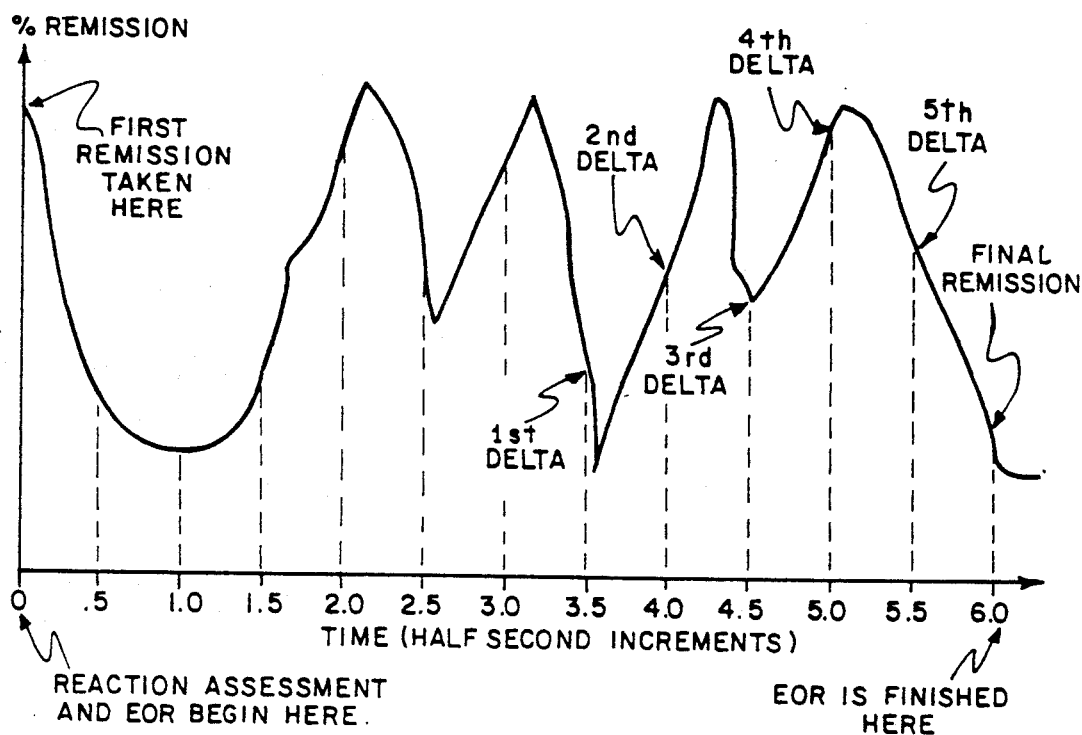
FIG. 12 illustrates another % remission versus time curve useful in understanding the operation of the software of the instrument of FIGS. 1-9.

Each time a comparison is made, the RAM location EORCOUNT is incremented by 1. EORCOUNT is zeroed at the beginning of this function. If so many comparisons are made that EORCOUNT equals IWMA, then EOR will have been reached. If this happens, and if the 4 bit RAM location ERS equals 1, then the 1 bit RAM location MAX_F is set. Otherwise MAX_F is cleared by this function, regardless of how this function terminates. An example of this type of EOR is given in FIG. 12. Here, IWMA equals 5. After five comparisons (deltas) are calculated and none of these deltas are found to be less than CRD, EOR is reached.

Once EOR has been found by reaching IWMA, then another remission is taken after TINC has elapsed. Following this remission, a Trace Check remission is read immediately. This remission is then written into RAM location EORREM1.

Regardless of how EOR was reached, this function now proceeds by outputing 4 bytes of EEH if the TRACE_F is set. This indicates to a PC that the function REACTION is completed.

The last thing REACTION does is to check if the EORREM1 value is greater than RAM number COL and less than RAM number COH. If EORREM1 is not between COL and COH then the SE_F bit in RAM is set. If EORREM1 is between COL and COH then the SE_F bit is not modified. It is possible that EOR was reached by finding a delta less than CRD, and that the last two remissions did not meet the CRD requirements but the last remission was within the limits set by COL and COH. In this case, a strip error is still considered to have occurred, and the SE_F bit remains set.

Throughout this entire function, the meter is alert for a pressing of the MEM button. If the MEM button is pressed, then a branch to the STRIP INTEGRITY function is performed. This terminates the Reaction Assessment function.

What is claimed is:

1. In combination, a strip supporting a reagent chemistry the remission of which changes as the chemistry reacts with a component of a body fluid to indicate the concentration of the component in the body fluid, the strip having opposed major surfaces, and a device for accepting the strip, the device comprising a pathway along which radiation is guided from a radiation source to the chemistry when the strip is properly inserted into the device and along which remission is guided from the chemistry to a radiation detector when the strip is properly inserted into the device, a tile having a tile surface for providing a standard remission, means for movably supporting the tile to permit the tile surface to move from a position in which the tile surface receives radiation from the radiation source and produces the standard remission which is guided along the pathway to the radiation detector when no strip is inserted into the device to a position separated from the radiation source by the strip when the strip is inserted into the device, the means for movably supporting the tile comprising a strip carrier body having a surface facing the tile, a lift for movable engagement by the strip carrier body, one of the strip carrier body and lift providing a pair of elongated slots the long dimensions of which extend generally transversely to the directions of motion of the strip into and from the device and generally transversely to the major surfaces of the strip when the strip is inserted into the device, the other of the strip carrier body and lift having a pair of oppositely extending trunnions for engaging the slots, the lift further including incline means for engagement by the strip as the strip is inserted into the device to move the lift away from the strip carrier body as permitted by the engagement of the trunnions in the slots and permit insertion of the strip between the strip carrier body and lift, the incline means provided at an entry end of the strip carrier body and lift, means for yieldably urging the lift toward the facing surface of the strip carrier body so that the lift lies against the facing surface of the strip carrier body when no strip is inserted into the device.

2. The combination of claim 1 wherein one of the lift and tile further includes a pair of opposed, aligned holes extending generally transversely to the directions of motion of the strip into and from the device, the axes of the holes extending generally parallel to the major surfaces of the strip when the strip is inserted into the device, the other of the lift and tile including a pair of oppositely extending second trunnions for engaging the holes to mount the tile pivotally from the lift.

3. The combination of claim 1 wherein the tile and the strip carrier body surface facing the tile are so shaped that the tile surface is spaced from the facing surface of the strip carrier body when no strip is inserted into the device and spaced from the strip when a strip is inserted into the device.

4. The combination of claim 1 and further comprising a housing for positioning the assembly including the strip carrier body, the lift and the tile, the housing including a second surface remote from, and generally parallel to, the strip carrier body surface facing the tile when the assembly including the strip carrier body, the lift and the tile is positioned in the housing, the lift and tile lying between the strip carrier body surface facing the tile and the second surface, the means for yieldably urging the lift toward the strip carrier body surface facing the tile comprises a compression spring, and the compression spring bears against the second surface and at least one of the lift and the tile.

5. The combination of claim 4 wherein the housing includes a third surface lying adjacent, and extending generally parallel to, the strip carrier body, one of the third surface and strip carrier body being provided with a locating protrusion and the other of the third surface and strip carrier body being provided with a recess for receiving the protrusion to locate the strip carrier body, lift and tile correctly within the housing when the assembled strip carrier body, lift and tile are slidably inserted into the housing.

6. The combination of claim 5 wherein the protrusion and the relief are generally frustoconical.

7. The combination of claim 6 wherein the protrusion is provided on the third surface.

8. The combination of claim 1 further including a housing for positioning the assembly including the strip carrier body, the lift and the tile, wherein the housing further comprises means for supporting the radiation source, the pathway along which radiation is guided from the source to the chemistry when the strip is properly inserted into the device including a first slot formed in the strip carrier body surface facing the tile opposite the tile when no strip is inserted into the device and opposite the chemistry when a strip is properly inserted into the device, the first slot being located adjacent the means for supporting the radiation source for directing radiation from the radiation source onto the tile when no strip is inserted into the device and for directing radiation from the radiation source onto the chemistry when a strip is properly inserted into the device.

9. The combination of claim 8 wherein the housing further includes a second surface which lies adjacent the strip carrier body surface facing the tile when the assembly including the strip carrier body, lift and tile is inserted into the housing, the second surface lying adjacent the strip carrier body and extending generally parallel to the strip carrier body surface facing the tile, and a second pathway along which radiation is guided from a second radiation source to the strip when a strip is inserted into the device and along which remission is guided from the strip to a second radiation detector when a strip is inserted into the device.

10. The combination of claim 9 incorporated into an instrument for determining the concentration of the component of a body fluid and for indicating the determined concentration of the component to a user of the instrument, the instrument comprising an instrument case for the instrument's components including the device, one of the instrument's components comprising a printed circuit board, the housing, the first-mentioned and second radiation sources, and the first-mentioned and second radiation detectors being mounted on the printed circuit board.

11. The combination of claim 1 further including a housing for positioning the assembly including the strip carrier body, the lift and the tile, wherein the housing further comprises means for supporting the radiation source, the pathway along which remission is guided from the chemistry to the radiation detector when a strip is properly inserted into the device including a first slot formed in the strip carrier body surface facing the tile opposite the tile when no strip is inserted into the device and opposite the chemistry when a strip is properly inserted into the device, the first slot being located adjacent the means for supporting the radiation source for directing radiation from the radiation source onto the tile when no strip is inserted into the device and for directing radiation from the radiation source onto the chemistry when a strip is properly inserted into the device.

12. The combination of claim 8 or 11 wherein the housing includes a third surface which lies adjacent the strip carrier body surface facing the tile when the assembly including the strip carrier body, the lift and the tile is inserted into the housing, the third surface lying adjacent the strip carrier body and extending generally parallel to the strip carrier body surface facing the tile, the pathway along which remission is guided from the chemistry to the detector when a strip is properly inserted into the device including a second slot formed in the third surface adjacent the first slot.

13. The combination of claim 12 wherein the housing includes a fourth surface lying at a small, nonzero angle to the third surface, the pathway along which radiation is guided from the source to the chemistry when a strip is properly inserted into the device including a third slot formed in the fourth surface.

14. The combination of claim 13 wherein the fourth surface lies between the means for supporting the radiation source and the chemistry when a strip is properly inserted into the device.

15. The combination of claim 13 wherein the third slot lies between the source and the chemistry when a strip is properly inserted into the device.

16. The combination of claim 15 wherein the first slot lies between the third slot and the chemistry when a strip is properly inserted into the device.

17. The combination of claim 16 wherein the first slot lies between the chemistry and the detector when a strip is properly inserted into the device.

18. The combination of claim 17 wherein the second slot lies between the first slot and the detector.

19. The combination of claim 1 incorporated into an instrument for determining the concentration of the component of a body fluid and for indicating the determined concentration of the component to a user of the instrument, the instrument comprising an instrument case for the instrument's components including the lift, the tile and the strip carrier body, the case including a removable case portion having an exterior surface and an interior surface, the exterior surface lying on the outside of the case when the case portion is in its use orientation on the instrument, and the interior surface lying on the inside of the case when the case portion is in its use orientation on the instrument, one of the interior surface and the strip carrier body provided with a pair of generally pawl-shaped members which extend away from the interior surface and define between them a slot which opens into a somewhat triangular region near their ends remote from the interior surface, then closes back to its slot configuration, the other of the interior surface and the strip carrier body including a web portion having opposite sides from each of which project two, generally parallel guide ribs and, between the guide ribs of each pair, a projection for engaging the triangular region defined between the remote ends of the pawl-shaped members when the web portion is inserted into the slot.

20. The combination of claim 1 incorporated into an instrument for determining the concentration of a medically significant component of a body fluid and for indicating the determined concentration of the medically significant component to a user of the instrument.

21. The combination of claim 20 comprising an instrument case for the instrument's components including the device, the case defining an instrument exterior, the case including a holder for supporting the strip carrier body, lift and tile assembly and for aligning and orienting the strip carrier body, lift and tile assembly for sliding insertion into, and removal from, the instrument, the strip carrier body including a web region extending longitudinally of the directions of motion of the strip carrier body, lift and tile assembly into and from the instrument, a pawl provided on the web region, the pawl having a locking surface on the side thereof which projects first into the instrument and an inclined camming surface on the side thereof which retracts first out of the instrument, the holder including a pair of resilient fingers between which the web is slidably received when the strip carrier body is in the instrument, one of the fingers including a pawl receiving portion having an inclined face and a locking face, the pawl engaging in the pawl receiving portion with the locking surface of the pawl engaging the locking face of the pawl receiving portion and the inclined surface of the pawl engaging the inclined face of the pawl receiving portion.

22. In combination, a strip supporting a reagent chemistry which reacts with a component of a body fluid to indicate the concentration of the component in the body fluid, and a device for accepting the strip, the device comprising a pathway along which radiation is guided from a radiation source to the strip when the strip is inserted into the device and along which remission is guided from the strip to a radiation detector when the strip is inserted into the device, a housing for providing a first remission, the housing receiving radiation from the radiation source and producing the first remission which is guided along the pathway to the radiation detector when no strip is inserted into the device, the housing separated from the radiation source by the strip when the strip is inserted into the device, the first remission and the strip's remission respectively indicating the absence and the presence of the strip in the device, the strip having first and second opposed major surfaces, the strip's remission being the remission of said first major surface, said second major surface having a second strip remission different from the first strip remission, the radiation detector producing a first output in response to detection of the first strip remission and a second and different output in response to the second strip remission, the first strip remission and the second strip remission respectively indicating first and second orientations of the strip in the device.

23. The combination of claim 22 wherein the device further comprises a second radiation source, a second radiation detector, and a second pathway along which radiation is guided from the second source to the chemistry when the strip is properly inserted into the device and along which remission is guided from the strip to the second radiation detector when the strip is properly inserted into the device, the second radiation detector producing different outputs based upon differences in remission of the chemistry corresponding to different concentrations of the component in the body fluid.

* * * * *